United States Patent [19]
Bedbrook et al.

[11] Patent Number: 4,962,028
[45] Date of Patent: Oct. 9, 1990

[54] PLANT PROMOTORS

[75] Inventors: John R. Bedbrook, Piedmont; Caroline Dean, Alameda; Pamela Dunsmuir, Piedmont, all of Calif.

[73] Assignee: DNA Plant Technology Corporation, Mt. Kisco, N.Y.

[21] Appl. No.: 883,604

[22] Filed: Jul. 9, 1986

[51] Int. Cl.⁵ .............................................. C12N 15/00
[52] U.S. Cl. .................................................. 435/172.3
[58] Field of Search ............ 536/27; 435/172.3, 317.1, 435/253, 252.33, 320; 935/23, 6, 30, 35

[56] References Cited

U.S. PATENT DOCUMENTS 4,495,280  1/1985  Bujard et al. ........................ 435/6
4,518,690  5/1985  Guntaka .............................. 435/71
4,551,433  11/1985 DeBoer .............................. 435/253

OTHER PUBLICATIONS

Goodman et al., (1987) "Gene Transfer in Crop . . ." Science 236: 48–54.
Dunsmuir et al., (1983) "A Number of Different . . ." Nucleic Acids Research 11: 4177–4183.
Faccietti et al., "Light-Inducible expression . . ." Bio Technology 3: 241–246.
Herrera-Estrella et al., (1984) "Light-Induable . . ." Nature 12: 115–120.
DeBlock et al., (1984) "Expression of Foreign . . ." EMBO J 3: 1681–89.
Dean et al., (1985) "Linkage & Homology . . ." PNAS 82: 4964–68.
Dean et al. (1985), "Differential Expression . . ." EMBO J 4:3055–3061.
H. Weiher et al., Science, 219 626–631 (1983).
R. T. Fraley et al., Proc. Natl. Acad. Sci., 80, 4803–4807 (1983).
S. M. Smith et al., J. Mol. Appl. Genet., 1, 127–137 (1981).
A. Cashmore et al., Genetic Engineering of Plants, T. Kosuge ed., 29–38 (1983).
S. L. Berry-Lowe et al., J. Mol. Appl. Genet., 1, 483–498 (1982).
C. F. Wimpee et al., Plant Molecular Biology, R. B. Goldberg ed., 12, 391–401 (1983).
J. Bedbrook et al., Nature, 287, 692–697 (1980).
G. Coruzzi et al., J. Biol. Chem., 258, 1399–1402 (1983).
G. Coruzzi et al., EMBO J., 3, 1671–1679 (1984).
G. van den Broeck et al., Nature, 333, 358–363 (1985).
P. H. Schreier et al., EMBO J., 4, 25–32 (1985).
R. Broglie et al., Science, 224–838–843 (1984).
R. Broglie et al., Science, 224–838–843 (1984).

Primary Examiner—Charles F. Warren
Assistant Examiner—David T. Fox
Attorney, Agent, or Firm—Clinton H. Neagley

[57] ABSTRACT

Promoter sequences from the gene from the small subunit of ribulose-1,5-bisphosphate carboxylase are disclosed. Expression cassettes containing a promoter sequence, a linker region, and a 3' fragment are also disclosed. The promotor sequences and expression cassettes are useful for expressing foreign genes to high levels in transformed plants.

14 Claims, 6 Drawing Sheets

```
SSU301  AAACAAAAA.................................AAGAAAAATTATATACATAAAAAATGGTTTGCAAAAGGACCTA..
SSU611  TGGCAAAACTGAAACTGAAAATGACGCCATCAAGAAAA..TATATGTCCGGACCCTC..TGCAAAGGAATGGTCTCTCCAAGTGCAA
SSU491  AATAATAATAATAATAATACAGTAAAGTTTTCAAGTTATAATAATAATAATAATAAGCTAACATTTCCAAATTTATTGTGCAT
                                                    16
SSU911  ATATTTGGATATATACAGTAAAGTTTTCAAGTTATACAGAATTTAAACTAAGCTAACATTTCCAAATTTATTGTGCAT
                                     15
SSU301  .AAAAGAATTAAGTTACCTCGATCACAC..
SSU611  TAAAGAA........CACACTGCAAATACAGCCAGTGTAGATGAGGCTAACCTCCTTTCTGAAAACACAGAAA
SSU491  GATTATCTTTTAAAATTCTGTGCCTCTGCCTCTTTACAAAAGAATTAACTTGTTCTATTAGTTACAAATAATAAGCGGGCAAATATT
SSU1112 AAGCTTTGGAGCCAACTATATGAATCTTT...CT.ATT.AAGTTCAGATATTTGTT.AAAAGTGATTAAAATTGT
SSU911  CTGACCTTGGC.......TATATGAATCCTTAAAATATCTTATTAAAGTTCTAAAATTATCATA.AAAAA.TGAAAAAC.TTGT
                                                            13
SSU301  ..........ATTCATATATCCACTTCCTACTCCATA............................TCGGATGAGATAAGATTACTAAGTGCT
SSU611  AATTAACCAACCATTCATATCCTCTTCCTACCCATT................................TCGGATGAGATAAGATTATTGAGCTAC
SSU491  TTATTCAAAAATACATGCCCCATTGATTAGTTTGAGGATTTTGC................................GATAAGGACTGAATGTAGT
SSU1112 CCTTCTAAAATTAAGAACAATAAGCGGCAAATATTTATTTAATAAGAGTTCGGAATTTTGAGATAAGATAAGGAATGAGTGTTAT
SSU911  CCGTCGATCTAAGTTTTAGACATAATAAAAACATATTCCATTCATTTAATTTGAAATGTTAA.GATAAGACTGAGTGTAGT
                                  14                                                    10
SSU301  TC.CACGTGGCACCTCCATTGTGGTGACATAATGAAGAGGGTCTTAGCTCC...AAAAATA.CATTCCAACC..TTTCAT
SSU611  TGACACGTGTCACCTCCATTCTGGTTAGTAGTGAAAAAAATGGGCTCATAGCTCATAAAATATCATTTCTC....TTTCAT
SSU491  GTCAGGGTTAAAA...........................................TTCAT
SSU1112 TTCAGGGGTTAAAA...........................................TTCAT
SSU911  GCGAGGGTTAAA.............................................TTCAT
                12                                             11                    6
SSU301  GTGTGGATATTAAATTTGTAAATATCAA...........TAATCCAATGCGTTAGCTTTACTCCAAGA..
SSU611  GTGGCCATTAAC....TTTGTAAAATCAA..........TAATGCAAAGTTTACGTTATCATTAGGAAG
SSU491  GTGGCCACCAAT..TTAGTAAATGTCAA...........TTATCCAAATGGTTACCATTCCTCGGCTTTA
SSU1112 GTGGCCACTAAT..TTTGTAAATGTCAA...........TAATCC.AATGTTACAATTCCTCTAATT.
SSU911  GTGGGCCTTCAATTTAGCAAT..TCAAGAACCAGTGAACCACCACACCACATAAT.CCAAAT.GTTACCGTTCCTCTA..
                9                                8                    7
```

FIG._IA.

```
                                                                    2                       1
                    TATGTGAAATATGTAAAAACCTTATCATTATATAAAGGG
                                                  TATGTGAAA............CCTTTTCATTATATATAGGA
                                                  TATGTGAAA..........CCTTATCACTATAAATAGAA
                                                  ..GTGAAA..........CTTATCATTATAAATAGAG
                                                  AIGTACAA..........CCTTATCACTATAAATAGAT
SSU301  ...GAGGTTAGTTGATTT.TTGTCCGTTAGA.........
SSU611  T..AGATGAGGTTTCCTTCCACTTGTGTCCGTTAGGTTAAATGGGAAAGAGA
SSU491  AGATGAGGTTTCCTTGT..TTGTGTCCGTCAGATGGAGAACGATATGTGAAA
SSU112  AGATGAGGTTTGTCGATTTGTGTCCGTTAGATGAGAGAAAAGG.
SSU911
         5                        4                        3

SSU301  TGTGGTGGGCAATACAAAAGTCAGTGTGAAGTGTTTAAAGGAAGAACAAAAATCTTCTAACTATG
SSU611  CAGGAGTCATAGTGCAATGACCATCATAAAGCA
SSU491  GTGGGACTAGGAAGCAAGGAAGGACCATTGACCCTCTTGAGAACAAAGCTCAAGGGAACCAAGGATTTATTTTCAGAA..   ATG
SSU112  GGGAAGACTAGGAAGGGGAATACCCGGCCAATAACTTTTCTAAGGATATTTCAGCA........               ATG
SSU911  ATTGCAAATGTCAAGGGAAGCAATAGCAATTATATTTAGCA                                       ATG

FIG_2.

PLANT PROMOTORS

FIELD OF THE INVENTION

This invention relates to gene expression, and to the regulation of gene expression, in plants. In particular, the invention relates to DNA promoter sequences, and to expression cassettes containing the sequences, which can be introduced into plants for purposes of regulating transcription of associated coding sequences. In addition, the invention relates to expression vectors which contain such expression cassettes and which are of use in transforming plants.

BACKGROUND OF THE INVENTION

A promoter is a sequence of DNA which can affect or control the level of transcription and which is responsible for (or provides the site for) the binding of RNA polymerase. The position of a promoter is fixed relative to the transcription start site within the genome of an organism. RNA polymerase is an enzyme (or a class of enzymes) which can bind to a promoter and bring about transcription of the structural gene (coding region) that is under control of the promoter, resulting in the production of messenger RNA (mRNA). Messenger RNA in turn provides the template for synthesis of polypeptides (translation).

Promoters have been studied in a variety of organisms, including viruses (e.g., U.S. Pat. Nos. 4,495,280, 4,518,690); bacteria (e.g., U.S. 4,551,433); plants; and animals. For a given species or type of organism, conserved regions of DNA (consensus sequences) have been found within promoters associated with a variety of structural genes. These regions are believed to be involved in the role played by the promoter in the transcription process.

Initiation of the transcription process in plants involves the interaction of a promoter with RNA polymerase II. Consensus sequences within plant promoters have been found at positions upstream from the 5' end of the transcription start point. There is a sequence of about seven base pairs positioned approximately 19-27 base pairs upstream of the transcription start point (i.e., positions −19 to −27) which is known as the TATA sequence, believed to play a role in RNA polymerase entry. There is another sequence of about nine base pairs positioned approximately 70 to 80 base pairs upstream from the transcription start point which is known as the CAAT box, believed to be involved in the regulation of the level of transcription. Other regions upstream of the transcription start point have been identified which affect the frequency of initiation of transcription in eukaryotes. These DNA sequences, known as enhancers or viral enhancer elements, have been found to affect the activity of promoters in their vicinity; these sequences are not promoters, as defined herein, in that their position need not be fixed. See H. Weiher et al., *Science*, 219, 626-631 (1983).

There have been studies of the introduction into plants of bacterial genes fused to bacterial promoters, resulting in expression of the bacterial gene in the plant. These introductions have involved the insertion of foreign DNA into the Ti plasmid of *Agrobacterium tumefaciens*, and the introduction of the foreign DNA into plants using Agrobacterium containing the modified Ti plasmid. See, e.g., R. T. Fraley et al., *Proc. Natl. Acad. Sci.*, 80, 4803-4807 (1983).

In order to provide high levels of expression of foreign genes in plant cells it is desirable to isolate the promoter regions from strongly expressed plant genes and use these fused with the foreign gene coding sequence to direct high levels of expression. Certain polypeptides known to be highly expressed in plants have been the subject of considerable study. One of these is the small subunit of the enzyme ribulose-1,5-bisphosphate carboxylase (RuBPCase). RuBPCase is the primary enzyme of the carbon fixation pathway in chloroplasts of plants of the C3 class. The enzyme consists of two types of polypeptide subunits, the small subunit (SSU) and the large subunit (LSU), eight of each of which assemble to give one molecule of RuBPCase. The small subunit, molecular weight approximately 14,000, is nuclear encoded and synthesized in the cytoplasm as a higher molecular weight precursor which includes a portion called the transit peptide. The precursor is transported into the chloroplasts via the mediation of the transit peptide. The precursor is processed to the mature subunit by post-translational mechanisms. The large subunit, molecular weight approximately 55,000, is encoded by chloroplast DNA and synthesized inside the chloroplast. The small subunit and large subunit are assembled in the chloroplast to yield RuBPCase.

RuBPCase is known to accumulate in response to light and studies have shown that there is a corresponding increase in the steady state levels of SSU mRNA resulting from increased transcription of the SSU gene. S. M. Smith et al., *J. Mol. Appl. Genet.*, 1, 127-137 (1981) Studies have also shown that there are multiple copies of the SSU gene in the nuclear DNA of various plant genomes, including petunia (P. Dunsmuir et al., *Nucleic Acids Res.*, 11, 4177-4183, 1983); pea (A. Cashmore et al., *Genetic Engineering of Plants*, T. Kosuge ed., 29-38, 1983); wheat (S. L. Berry-Lowe et al., *J. Mol. Appl. Genet.*, 1, 483-498, 1982); and Lemna (C. F. Wimpee et al., *Plant Molecular Biology*, R. B. Goldberg ed., 12, 391-401, 1983).

In early work on the isolation of a cloned cDNA for the SSU gene in pea, there was a report of the sequence of a clone p20 corresponding to 123 amino acids of mature SSU, 13 amino acids of transit peptide, and 260 nucleotides of 3' non-coding region. J. Bedbrook et al., *Nature*, 287, 692-697 (1980). Subsequently, there were reports of sequence information for another pea cDNA clone, pSS15, and the corresponding genomic fragment pPS-2.4. G. Coruzzi et al., *J. Biol. Chem.*, 258, 1399-1402 (1983); G. Coruzzi et al., *EMBO J.*, 3 1671-1679 (1984). The isolation and characterization of petunia cDNA clones pSSU41, pSSU51, pSSU71, and pSSU117 and sequence information corresponding to part of the mature peptide region plus the 3' untranslated region for cDNA clones pSSU51 and pSSU117, was reported in P. Dunsmuir et al., *Nucleic Acids Res.*, 11 4177-4183 (1983).

There have been reports of reintroductions into tobacco cells of promoter regions derived from pea SSU genes fused to bacterial gene coding regions. The introduction into tobacco, and expression, of a chimaeric gene consisting of the 5' region (promoter) of pea SSU gene labelled SS3.6 plus the coding region of the bacterial chloramphenicol acetyltransferase (CAT) and the 3' region of nopaline synthetase (nos) was reported in L. Herrera-Estrella et al., *Nature*, 310, 115-120 (1984). In this report the 5' region was fused to the coding region at a position 4 nucleotides upstream from the transcription initiation site. Another report disclosed the fusion of promoter and transit peptide DNA (plus the first codon—methionine—of the mature peptide region) from pea SSU gene SS3.6 to the structural gene for the bacterial protein neomycin phosphotransferase II, the introduction of the fused gene into tobacco plants, and the transport of the structural gene to the chloroplast in transformed plants. G. van den Broeck et al., *Nature*, 333, 358–363 (1985). A similar disclosure appears in P. H. Schreier et al., *EMBO J.*, 4, 25–32 (1985), except that the promoter-transit peptide component contained additional DNA including the first 22 codons of the SSU mature peptide. There has also been a report of the introduction of DNA for pea SSU gene labelled pS4.0 into petunia, under the control of its own promoter, to yield heterologous RuBPCase containing pea SSU and petunia LSU. R. Broglie et al., *Science*, 224, 838–843 (1984).

SUMMARY OF THE INVENTION

In accordance with the invention, a new promoter system is provided which may be used to express foreign structural genes in plants (the word "foreign" meaning that the structural gene does not naturally occur in association with the promoter in question). The invention is based on the discovery of and isolation from Petunia (Mitchell) of highly efficient SSU promoter DNA, in particular the promoter DNA from the SSU gene denominated SSU301. The invention embraces the promoter DNA, DNA substantially homologous to the promoter DNA, and DNA at least in part substantially homologous to the promoter DNA. The invention further embraces the promoter in several forms: the promoter as an isolated 5' fragment of the SSU gene; the promoter as an isolated 5' fragment with the 3' end of the 5' fragment modified to create a restriction site which permits ready fusions with foreign structural genes; and the promoter in the form of an expression cassette comprising a 5' fragment of the SSU gene, a 3' fragment (preferably from the SSU gene), and a linker region connecting the two fragments. In particular, the invention is such an expression cassette where the fusion points between the 5' fragment and the linker region and between the 3, fragment and the linker region have been modified to create restriction sites which permit a foreign gene to be substituted for the linker so as to yield chimaeric genes containing the complete proximal 5' and 3' regions of the SSU gene but containing none of the DNA normally found between the translation start and stop sites of the SSU structural gene. The expression cassette of the invention preferably comprises at least 300 bp (base pairs) of both SSU 5' region and SSU 3' region. In a preferred embodiment the expression cassette of the invention contains a linker region bounded by 5' DNA and 3' DNA from SSU301, with an NcoI restriction site immediately upstream of the linker region and a BglII restriction site immediately downstream of the linker region (ATCC #67125). The invention also embraces chimaeric genes, or fused genes, resulting from the substitution via restriction enzymes of a foreign gene for the linker region of the expression cassettes of the invention. The invention further comprises expression vectors containing the expression cassettes of the invention or containing the expression cassettes of the invention with a foreign structural gene substituted in place of the linker region. In addition, the invention embraces the methods of preparing and using the promoters and expression cassettes of the invention.

BRIEF DESCRIPTION OF THE DRAWINGS

FIG. 2 is a depiction of DNA sequence information for the 3' region of a gene for the small subunit of Petunia ribulose-1,5-bisphosphate carboxylase.

DETAILED DESCRIPTION

As used herein, the term "gene" means coding region together with associated 5, and 3, sequences. The term "structural gene" means coding region. The term "SSU gene" means the SSU structural gene plus an upstream DNA sequence (5' untranslated region) and a downstream DNA sequence (3' untranslated region). The upstream DNA sequence may also be referred to herein as the SSU promoter sequence, SSU promoter DNA, SSU promoter, SSU 5' sequences, SSU 5' region, SSU 5' fragment or SSU 5' flanking region. The upstream DNA sequence has one terminus corresponding to the nucleotide adjacent (on the 5' side) to the translation start site (ATG), and runs upstream from there. The downstream DNA sequence may also be referred to herein as the SSU 3' region, SSU 3' sequence, SSU 3' flanking region, SSU 3' fragment or SSU 3, tail. The downstream DNA sequence has one terminus corresponding to the nucleotide adjacent (on the 3' side) to the translation stop site (TAA) and runs downstream from there. The term "SSU structural gene" means a DNA sequence encoding the SSU precursor polypeptide, i.e., the SSU mature peptide plus the associated transit peptide. The DNA coding sequence has the translation start site at one terminus (5' terminus) and the translation stop site at the other (3' terminus).

A genomic library was constructed from DNA found in leaf cells of Petunia (Mitchell). The SSU301 gene and the SSU611 gene, along with five others from the group of eight SSU genes, were isolated from the genomic library using probes made from petunia SSU cDNA clones. The individual genes were identified after hybridization and high stringency washing to the different cDNA clones. The 5' and 3' ends of the isolated genes were sequenced using the dideoxy sequencing method. See Example II.

For purposes of evaluating promoter sequences of the invention, DNA probes were constructed specific to SSU genes found in the nuclear genome of Petunia (Mitchell). Probes made of 3' flanking regions discriminated among genes which were in what shall be referred to as three different gene families, namely, families corresponding to cDNA clones pSSU51, pSSU71 or pSSU117 (these gene families shall be referred to herein as, respectively, the 51 gene family, the 71 gene family, and the 117 gene family). As explained further below, the 51 gene family contains six of a total of eight SSU genes in petunia, the 71 gene family contains one SSU gene (SSU301), and the 117 gene family contains one SSU gene (SSU611). These probes were used to determine relative expression of the different gene families, based upon hybridization with mRNA. The highest level of steady state mRNA was found for mRNA corresponding to the gene for SSU301 (the sole gene in the 71 family). The second highest level corresponded to the gene for SSU611 (the sole gene in the 117 family). See Example III.

Figure 1:
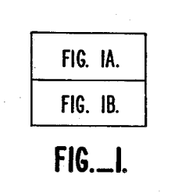
FIGS. 1A and 1B are a depiction of DNA sequence information for the 5' region of a gene for the small subunit of Petunia ribulose1,5-bisphosphate carboyxlase.
Figure 1A:
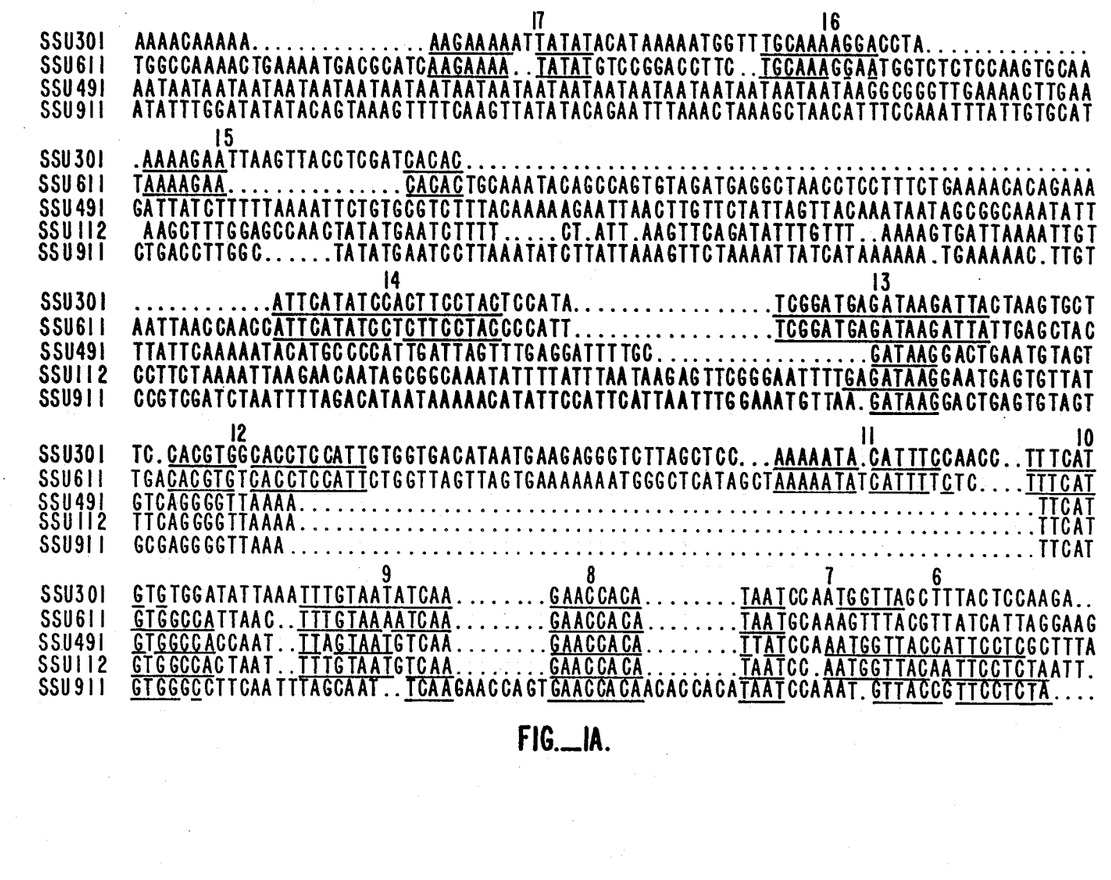
Figure 1B:
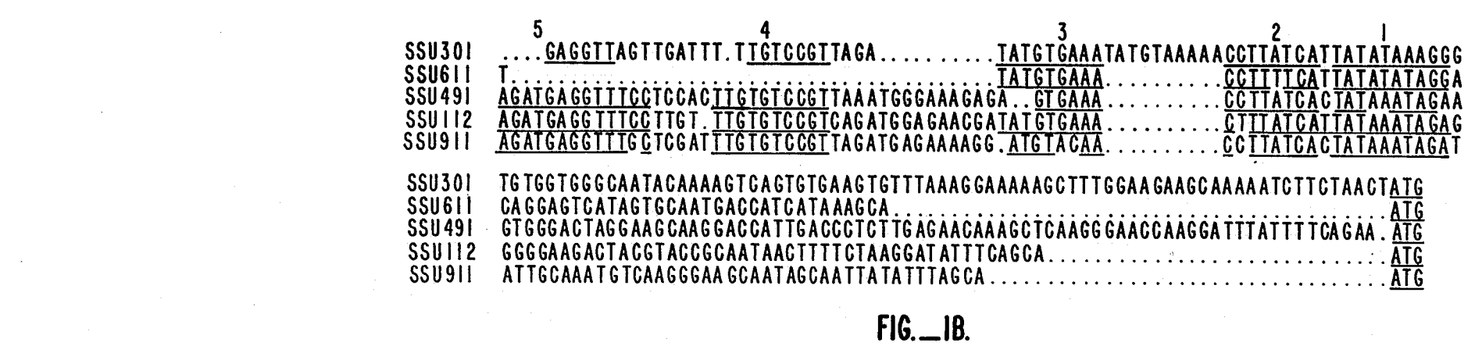

The sequence of the 5' untranslated region of the SSU301 an SSU611 genes, together with the corresponding regions of five others from the group of eight SSU genes, is shown in FIG. 1 (SSU491, SSU112, and SSU911 correspond to genes from the 51 family). The final three bases shown for the 5' region of each gene (lower right of FIG. 1) correspond to the translation start signal (ATG). The sequences for the different genes are organized so that the regions of homology are aligned. All of the sequences show an A or G positioned 3 bases upstream from the ATG start signal; this is believed related to efficient translation of a message. Regions which are conserved or semiconserved among the different 5' sequences are shown by underlining and numbering of block areas (numbers 1-17 on top of rows of sequences). Block 1 shows a putative TATA box homology. Since the TATA homology is normally positioned approximately 30 bp upstream from the transcription start, the 5' leaders (the segments between the transcription start and the translation start) appear to be fairly short (between 10 and 60 bp). The transcription start for the SSU301 gene is 54 bp 5' to the ATG translation codon. Block 7 shows a possible CCAAT box homology. There are also sequences containing homology to the 'core' nucleotides of viral enhancer elements, e.g., block 8.

The sequence of the 3' untranslated region of the SSU301 and SSU611 genes, together with the corresponding regions of others from the group of eight SSU genes, is shown in FIG. 2 (SSU231, SSU491, SSUI112, SSU911 and SSU211 correspond to genes from the 51 family). The initial three bases shown for the 3' region of each gene (upper left of FIG. 2) correspond to the translation stop signal (TAA or TAG). Regions which are conserved or semiconserved among the different 3' sequences are shown by underlining and numbering of block areas (numbers 1-10 on top of rows of sequences). Block area 7 is likely a signal for polyadenylation. Differences in the 3' regions of the genes may lead to mRNA stability and thus affect the steady-state levels of mRNA.

It was initially demonstrated that the SSU promoter DNA of the invention functions upon reinsertion into plants in association with the wild type SSU structural gene. See Example IV.

It was subsequently demonstrated that the SSU promoter DNA of the invention can be used to control expression of foreign structural genes by introducing the promoter DNA and structural gene into the plant as a unit. This may be accomplished by fusing the promoter DNA directly to the structural gene prior to introduction into the plant. This is preferably done with the SSU promoter (in particular, the SSU301 promoter), not including the translation start codon at the promoter's 3' end, fused directly to the translation start codon of the structural gene. For this purpose the SSU promoter is preferably modified in advance to create a restriction site at the 3' end such that the applicable restriction enzyme will cleave at a point at or immediately upstream of the translation start codon in the wild type SSU gene (as explained further below in the discussion of expression cassettes). The fusion of the promoter DNA can either be to the structural gene containing its wild type 3' tail (if the structural gene is eukaryotic) or to a structural gene with a substituted 3' tail, preferably SSU 3' region and in particular SSU301 3' region. The SSU promoter DNA for use in fusion to a structural gene should be a segment at least 300 bp in length, and preferably at least 1000 bp in length. Longer lengths can effectively be used up to approximately 5000 bp. Even longer lengths can be used but may detract from experimental workability. If a substituted 3' SSU region is used in preparing the fused gene, this region should be at least 300 bp in length and preferably 1000-5000 bp in length.

In accordance with the invention, a preferred way to accomplish introduction of SSU promoter DNA and a foreign structural gene into a plant is to initially combine the foreign gene with an expression cassette comprising SSU promoter DNA (in particular SSU301 promoter DNA), a linker region fused downstream of the SSU promoter DNA, and SSU 3' region DNA (in particular SSU301 3' DNA) fused downstream of the linker region. In a preferred expression cassette, the 3' end of the promoter DNA and the 5' end of the 3' fragment are modified to create restriction sites such that the applicable restriction enzymes can cleave the cassette, respectively, at a point immediately upstream of the position of the translation start codon in the wild type SSU gene and at a point immediately downstream of the position of the translation stop codon in the wild type SSU gene. Hence the linker region may be removed by restriction enzyme cleavage and replaced by a fragment containing the gene to be introduced.

In the case of an expression cassette derived from SSU301, which is particularly preferred, the 3' end of the promoter can be modified in various ways to create a restriction site at the desired position. A preferred modification is to change the T nucleotide immediately upstream from the translation start codon of the wild type SSU301 gene to a C nucleotide, thereby yielding a six-base sequence CCATGG surrounding the translation start codon of the wild type SSU301 gene; this sequence corresponds to the restriction site for the restriction enzyme NcoI (see FIG. 3). Application of NcoI to a sequence so modified will cleave immediately upstream of the start codon (ATG) of the SSU gene. Other restriction sites could be created at the position just upstream of the translation start codon, with preferred modifications involving the fewest number of base changes. For instance, as will be understood by one skilled in the art, restriction sites specific to restriction enzymes NdeI or SphI could be created by appropriate DNA modifications (these enzymes also cleave around the sequence ATG which is the first codon of the coding region). Similarly, modifications can be made to the 5' end of the 3' fragment in an expression cassette derived from SSU301. A preferred modification is to change the T nucleotide two positions downstream from the translation stop codon of the SSU gene to an A nucleotide and to change the A nucleotide 4 positions downstream from the translation stop codon to a C nucleotide, thereby yielding a 6-base sequence AGATCT on the downstream side of the stop codon; this sequence corresponds to the restriction site for the restriction enzyme BglII (see FIG. 3). Application of BglII to a sequence so modified will cleave immediately downstream of the stop codon. Other restriction sites could be created at the position just downstream of the translation stop codon, with preferred modifications involving the fewest number of base changes. For instance, as will be understood by one skilled in the art, restriction sites specific to restriction enzymes EcoRV, HincII or HpaI could be created by appropriate DNA modifications. See Example V herein with respect to preparation of the particular preferred expression cassette referred to above.

Nucleotide modifications to the promoter and 3, sequences as described above are carried out using known techniques. Mutations are generated by known methods of site-directed mutagenesis using oligonucleotides (the sequences of which contain the desired mutation) and single stranded template DNA of the promoter and 3' sequences. See, e.g., M. J. Zoller et al., *Nucleic Acids Res.*, 10, 6487–6500 (1982).

The linker sequence of the expression cassette of the invention is a noncoding segment of DNA inserted between the promoter region and the 3' region of the expression cassette. The sequence preferably has terminal restriction sites corresponding to those at the sites to which the linker is to be joined. Thus, for an expression cassette derived from SSU301 modified to have an NcoI restriction site at the end 3' to the promoter sequence and a BglII restriction site at the end 5' end to the 3' sequence, the linker would have a corresponding NcoI restriction site at one end and a corresponding BglII restriction site at the other. Ligation of the linker sequence to the end segments is by standard techniques. The length of the linker sequences is not critical; the length is preferably between 200 and 1000 bp.

The expression cassette contains at least 300 bp of promoter sequence upstream from the translation start site and at least 300 bp of 3' sequence downstream from the translation stop site, with at least 1000 to 1500 bp preferred in each case. Longer lengths can effectively be used in each case, up to approximately 5000 bp. Even longer lengths can be used in each case but may detract from experimental workability. The expression cassette preferably has a restriction site at each terminus (i.e., at the 5' end of the promoter sequence and at the 3' end of the 3' sequence) to allow the cassette to be separated from a vector as a linear DNA sequence.

A foreign gene may be introduced into the expression cassette of the invention in place of the linker sequence by cleavage of the expression cassette at the restriction sites on either side of the linker sequence and ligation of the foreign gene to the ends of the expression cassette so that the translation start codon of the foreign gene is proximal to, and preferably immediately adjacent to, the 3' end of the promoter sequence of the expression cassette and so that the translation stop codon of the foreign gene is proximal to, and preferably immediately adjacent to, the 5' end of the 3' sequence of the expression cassette.

Once the foreign gene is inserted in the expression cassette, the expression cassette can be introduced into an appropriate plant transformation vector, and plant transformation carried out using known techniques, e.g., with Agrobacterium. A plant so transformed will contain the foreign gene under transcriptional control of the SSU promoter. See Example VI.

The SSU promoters of the invention, in particular in the form of the expression cassettes of the invention, can be used to introduce foreign structural genes, regardless of type or source, into plants which are transformable.

Figure 5:
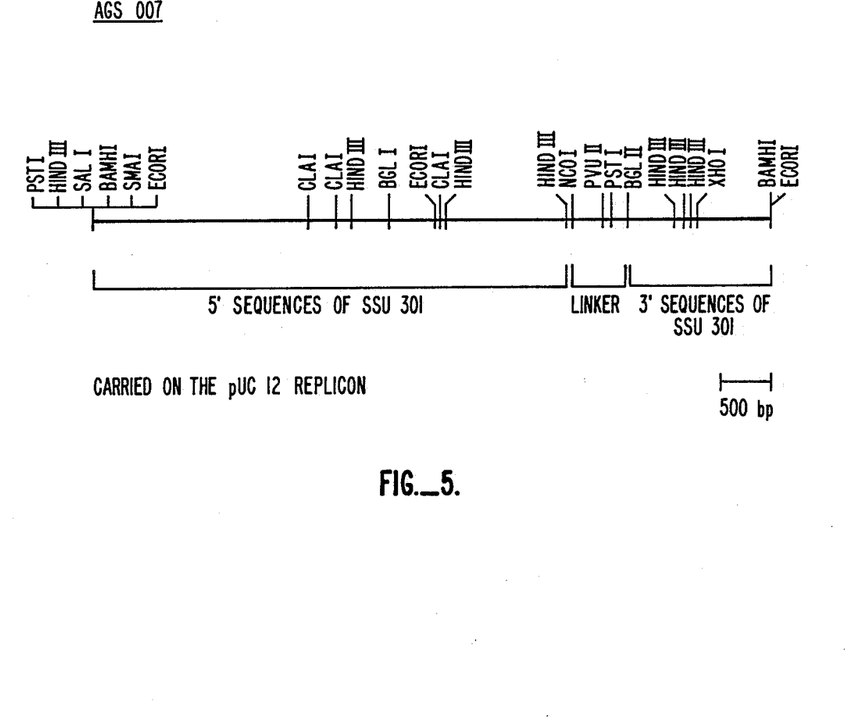
FIG. 5 is a schematic showing restriction information for recombinant plasmid pAGS007 containing an expression cassette of the invention (ATCC deposit #67125).

A preferred expression cassette of the invention contains SSU301 promoter DNA (5000 bp approximately) with an NcoI restriction site at its 3' terminus, SSU301 3' region DNA (1500 bp approximately) with a BglII restriction site at the 5' terminus, and an intervening linker region (600 bp approximately). The expression cassette is bordered by BamHI restriction sites. Such a cassette is on deposit at the American Type Tissue Culture (deposit number 67125). The deposited microorganism is *E. coli* JM83-AMB007, a gram-negative, rod-type strain. This strain contains recombinant plasmid AGS007, which is a pUC plasmid (specifically, pUC12; J. Veira et al., *Gene*, 19, 259–268, 1982), carrying the expression cassette. See FIG. 5 for a schematic of plasmid AGS007 carrying the expression cassette. The expression cassette may be obtained from this deposited sample, as will be understood by those skilled in the art in view of the disclosure herein, by separating recombinant plasmid pUC12 from *E. coli* and isolating the expression cassette from the plasmid by using the restriction enzyme BamHI. If desired, the promoter sequence can be obtained from the expression cassette using the restriction enzyme NcoI and BamHI. This will yield restriction fragments of approximately 5, 2.7 and 2.1 kb. The 5 kb fragment will carry the promoter region. The linker region in the deposit is the 600 bp NcoI-BglII fragment from the NPTII gene carried on Tn5.

EXAMPLES

In general, preparation of plasmid DNA, restriction enzyme digestion, agarose gel electrophoresis of DNA, Southern blots, Northern blots after separation of the RNA on a formaldehydeagarose gel, DNA ligation and bacterial transformation were carried out using standard methods. Maniatis et al. (ed.), *Molecular Cloning, a Laboratory Manual*, Cold Spring Harbor Laboratory (1982).

EXAMPLE I

Isolation of SSU301 Gene

A. Plant material

The Petunia (Mitchell) strain is a doubled haploid produced by another culture from a hybrid between *Petunia hybrida* var Rose of Heaven and *Petunia axillaris* (A. Z. Mitchell, Dissertation, Harvard Univ., 1979). The plants were grown under greenhouse conditions.

B. Isolation of DNA

Petunia DNA was isolated as described in P. Dunsmuir et al., *J Mol. Appl. Genet.*, 2, 285–300 (1983).

C. Preparation of Genomic Library

Petunia DNA was partially digested with Sau3A to give a mean fragment size of 15–20 kilobases (kb). The DNA was then fractionated on a 10–40% sucrose gradient with 1 M NaCl/20 mM Tris-HCl, pH 8/1 mM EDTA. The gradient fractions containing DNA fragments between 15 and 20 kb were concentrated with butanol and then by ethanol precipitation. Lambda phage EMBL3 DNA was completely digested with BamHI and then digested with a 10-fold excess of EcoRI. This step allows a biochemical selection against the reinsertion of the phage stuffer fragment during the ligation reaction. The small linker fragment was removed by isopropanol precipitation. A. M. Frischauf et al., *J. Mol. Biol.*, 170, 827–842 (1983). The double-cut EMBL3 DNA was ligated to the fractionated petunia DNA in a 2:1 molar excess of EMBL3. Ligated DNA was packaged into lambda phage heads in 0.75 ug (EMBL3) aliquots using the Hohn and Murray procedure B. Hohn et al., *Proc. Natl. Acad. Sci. USA*, 74, 3259–3264 (1977). Two phage banks (200,000 recombinant phage) were screened by hybridization W. D. Benton et al., *Science*, 196, 180–182 (1977).

D. Preparation of Probes

Probes were prepared for use in isolating the SSU301 gene from the genomic library. The probes were of two types. The first type was the complete cDNA clone SSU71, the preparation and characterization of which is described in P. Dunsmuir et al., *Nucleic Acids Res.*, 11, 4177–4183 (1983). The second type was the 3' untranslated region of the pSSU71 clone. The 3' region was obtained from the pSSU71 clone by restriction enzyme cleavage.

E. Isolation of Gene

The petunia SSU genes were isolated from a lambda phage genomic library using a petunia cDNA clone as a probe. See P. Dunsmuir et al., *Nucleic Acids Res.*, 11, 4177–4183 (1983) regarding cDNA clone construction. The SSU301 gene was identified from the other genes by hybridization after high stringency washing to the SSU cDNA clone pSSU71. This was confirmed by using a probe which only contained the 3' untranslated region of the cDNA clone pSSU71.

EXAMPLE II

Sequencing of SSU301, 5' and 3' Regions

A. Method

The SSU genes, carried in the lambda phage clones described in C. Dean et al., *Proc. Natl. Acad. Sci. USA*, 81 4964–4968 (1985), Were subcloned into pUC plasmids (J. Vieira et al., Gene, 19, 259–268, 1982). These plasmids were linearized at unique restriction sites at one end of the rbcS genes. Progressive deletions into the genes were generated using Bal31 nuclease (N. E. Biolabs). Conditions were standardized so that approximately 200 bp/min were deleted. After phenol extraction the samples were then digested with a second restriction endonuclease which cut the insert out of the plasmid. The insert fragments were subcloned into M13 phage (J. Messing et al., *Nucleic Acids Res.*, 9, 309–321, 1981) and the inserts were screened for their size. A range of inserts differing in approximately 100 bp were sequenced using the dideoxy sequencing method of F. Sanger et al., *Proc. Natl. Acad. Sci. U.S.A.*, 74, 5463–5467 (1977). The procedure was repeated for the other DNA strand by linearizing the plasmid at a restriction site at the opposite end of the gene and then creating progressive deletions into the gene in the other direction.

B. Results

Sequence information is shown for the 5' untranslated region (FIG. 1 and the 3' untranslated region (FIG. 2) for SSU301, SSU611 and several of the SSU genes from the 51 gene family.

EXAMPLE III

Activity of Promoters

Relative activity of SSU promoters was determined by isolating and quantitating SSU mRNA.

A. Plant Material

The plant material was the same as in Example I. Leaf material used in RNA extractions was harvested from plants about 10 weeks old: only the top young leaves were used. The other organs of the plant used in RNA extractions were harvested from plants 18 weeks old.

B. RNA Isolation

Two g aliquots of the plant material from which the RNA was to be isolated were frozen in liquid nitrogen in a mortar and pestle and ground to a fine powder. 4.5 ml of NTES buffer (0.1 M NaCl, 0.01 M Tris-HCl pH 7.5, 1 mM EDTA, 1% SDS) and 3 ml of a phenol/chloroform solution [a 1:1 mixture of Tris-buffered (pH 8) phenol with chloroform/isoamyl alcohol (24:1)] were added and the grinding continued until the mixture thawed. The mortar was washed with 4.5 ml of NTES buffer and 3 ml of the phenol/chloroform solution. After vortexing for 5 minutes, the solution was centrifuged at 20,000 g for 10 minutes. The aqueous phase was removed and the phenol/chloroform layer was washed with 2 ml of NTES buffer. The combined aqueous layers were phenol extracted twice more. The nucleic acid was then precipitated by the addition of 0.1 vol. of 2 M NaAc and 2 vol. of ethanol. The precipitate was washed with 70% ethanol and then resuspended in 2.5 ml of sterile water. To remove DNA and low molecular weight RNA, an equal volume of 4 M LiAc was added and the solution allowed to sit for 3 hours on ice. The precipitate was pelleted at 10,000 g for 10 minutes. The pellet was resuspended in 0.9 ml of sterile water and the RNA was precipitated by the addition of 0.1 ml 2 M NaAc and 2 ml of ethanol. The pellet was washed with 70% ethanol and then resuspended in 0.1×SSC. The yield of RNA from 2 g of leaf tissue was approximately 4 mg.

C. RNA Quantitation 2.5 ug aliquots of each RNA sample or a dilution series of RNA from leaf tissue were denatured in 40 mM phosphate buffer pH 6.8, 6% formaldehyde for 30 minutes at 65° C. The samples were then adjusted to 1 m NH$_4$Ac before loading onto a slot apparatus (8 × 1 mm slots). A sheet of Genescreen Plus (N.E.N.) rinsed in 1 M NH$_4$Ac was placed immediately beneath the slots. Whatman 3MM paper and paper towels were used beneath the Genescreen Plus filter to draw the liquid placed into the slots through the Genescreen Plus filter. After addition of the RNA samples the slots were rinsed with 200 μl 1 M NH$_4$Ac. The filters were dried and baked in a vacuum oven at 80° C. for 2 hours.

The 3' probes and the cDNA clone pSSU51 are inserts in the vector pUC9(J. Vieira et al., *Gene*, 19, 259–268, 1982) and can be cut out with a double enzyme restriction digest using EcoRl and HindIII. These were labelled with [alpha-$^{32}$]daTP (400 Ci/mmol) using the T$_4$ polymerase procedure of P. O'Farrell, *BRL Focus*, 3, 1–3 (1981) after digestion of the clones with EcoRl. Following labelling, the clones were digested with HindIII to cut out the 3' tail sequences. The labelled inserts were purified on a 5% polyacrylamide gel. Using this method only the DNA strand complementary to the mRNA was labelled. The resection and filling in of the DNA was optimized to ensure labelling of the entire insert. This yielded probes of the same specific activity.

Prehybridization, hybridization and washing conditions were as described in C. Dean et al., *Proc. Natl.*

Acad. Sci. U.S.A., 82 4964–4968 (1985). After exposure of the filters to Kodak X-ray film, the films were scanned densitometrically using a LKB Laser densitometer.

D. Results

The relative expression of SSU genes in Petunia leaf tissue is shown in Table I below.

TABLE I

| | A Hybridization To RNA | | B Number of cDNA clones | C Relative Expression of Each Gene (%) |
|---|---|---|---|---|
| | (1) | (2) | | |
| SSU301 | 1 | 1 | | 46.3 |
| SSU611 | 0.5 | 0.48 | 73 | 22.7 |
| SSU491 | 0.145 | 0.18 | 23 | 7.4 |
| SSU112 | } 0.15 | } 0.16 | 17 | 6.9 |
| SSU911 | | | 0 | N.D. |
| SSU231 | | | 6 | 1.9 |
| SSU211 | | | 6 | 1.9 |
| SSU511 | | | 42 | 13 |

Column A above shows the relative hybridization of the four rbcS 3' tail probes to petunia leaf RNA. Columns (1) and (2) summarize the results from two different RNA preparations. The gene showing the strongest hybridization signal is given the value of 1. The expression of the other genes is presented as fractions of this. The expression of the two rbcS genes SSU112 and SSU911 are given collectively, as the 3' tail probe 91A would hybridize to transcripts from both genes. Column B shows the number of cDNA clones isolated corresponding to each rbcS gene. These data were necessary to calculate the relative expression levels of the different rbcS genes because gene-specific probes could not be made for each individual gene due to the high degree of sequence homology. Column C shows the relative contribution of each rbcS gene to the total rbcS expression in leaf tissue (calculated from the data in columns A+B). N.D.=not detected. The genes SSU511 and SSU231 are indistinguishable over the sequence compared in the cDNA clone, hence individual expression levels could not be calculated for these genes.

Tests of relative expression of SSU genes in other Petunia organs (sepal, stigma/anther, petal, stem) gave results as shown in Table II below.

TABLE II

| Gene | Leaf | Sepal | Stigma/Anther | Petal | Stem |
|---|---|---|---|---|---|
| SSU301 | 1 (1) | 1 | 1 | 1 (1) | 1 (1) |
| SSU611 | 0.5 (0.44) | 0.63 | 0.15 | 0.27 (0.56) | 0.22 (0.17) |
| SSU491 | 0.14 (0.18) | 0.08 | 0.15 | 0.02 (0.06) | 0.03 (0.04) |
| SSU112 SSU911 | 0.15 (0.15) | 0.08 | 0.15 | 0.01 (0.02) | 0.03 (0.02) |

The relative hybridization of the four rbcS 3' tail probes to RNA isolated from different organs of petunia is summarized above. The gene showing the strongest hybridization signal has been allotted the value of 1. The expression of the other rbcS genes is then presented as fractions of this. The numbers in the brackets show results from a second experiment. In each experiment alkali-hydrolyzed RNA was used as a control to ensure that only RNA was contributing to the hybridization signal. The expression of the two rbcS genes SSU112 and SSU911 are given collectively as the 3' tail probe 91A would hybridize to transcripts from both genes.

EXAMPLE IV

Reintroduction of SSU301 Promoter Associated with the Wild Type SSU Gene

Figure 4:
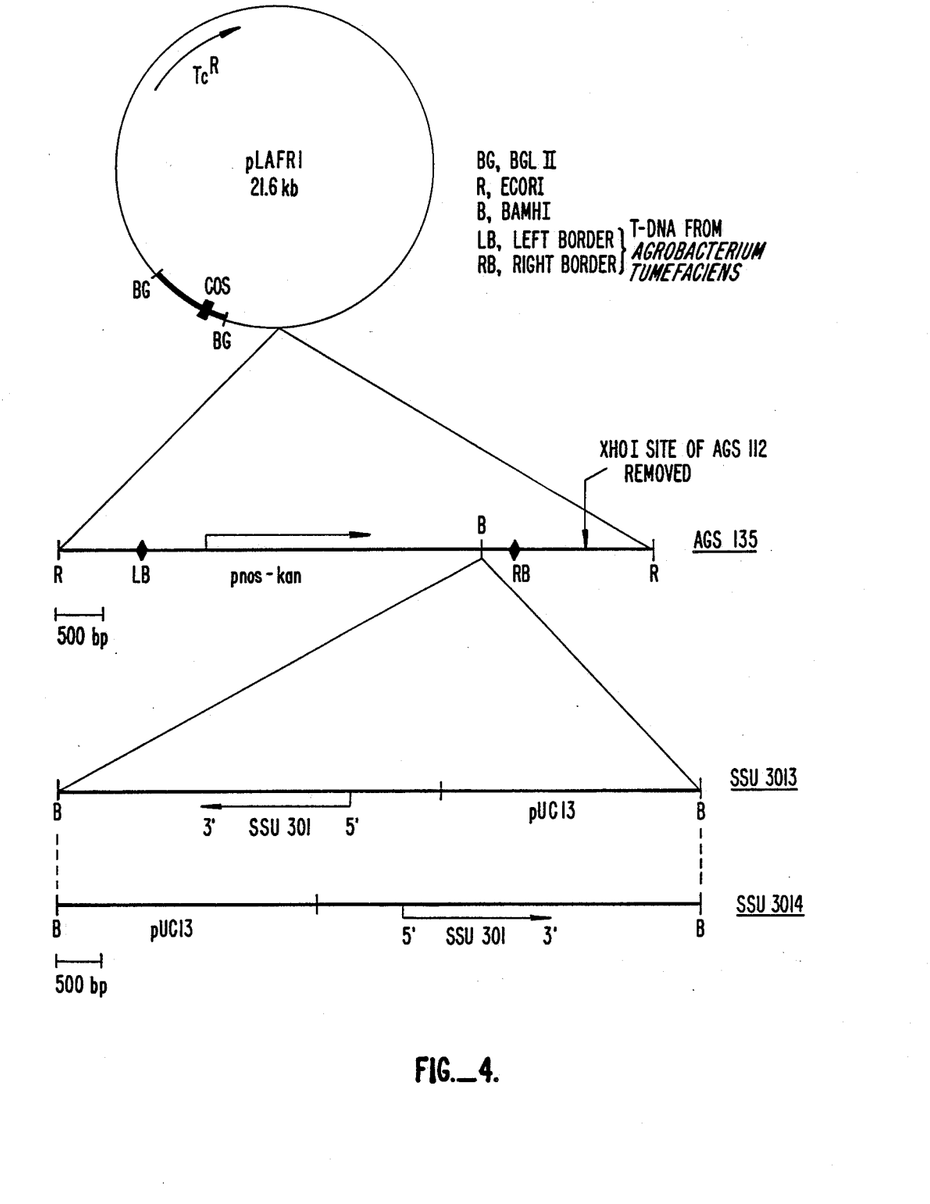
FIG. 4 is a schematic showing restriction information for DNA constructs SSU3013 and SSU3014.

The genomic clone SSU301 was introduced into binary vector pAGS135 by linearizing both plasmids at BamHI sites. The vector pAGS135 is the same as vector pAGS112 described in P. van den Elzen et al., Plant Molecular Biology, 5, 149–154 (1985) except that the unique XhoI site in pAGS112 has been removed by Klenow treatment of the linearized DNA and religation. Both orientations of the insert were conjugated into Agrobacterium tumefaciens LBA4404. The constructs pSSU3013 and pSSU3014 are illustrated in FIG. 4.

The constructs were introduced into tobacco cells by cocultivation and transformed calli were selected on kanamycin. Nine plants were regenerated for each construction and RNA was isolated from the young leaves after the plants had been in the greenhouse three weeks. The RNA was applied to slot blots and probed with the 3' specific probe 30A. Controls on the slot blot included non-transformed tobacco which showed that the 30A probe did not hybridize to tobacco RNA and untransformed petunia RNA which showed the endogenous level of SSU301 expression. Six of the 18 tobacco transformants showed levels of SSU301 RNA equivalent to that found in petunia. Seven of the 18 showed levels 50% or less than in petunia and 5 showed very low or undetectable levels.

EXAMPLE V

Construction of SSU Expression Cassette

Figure 3:
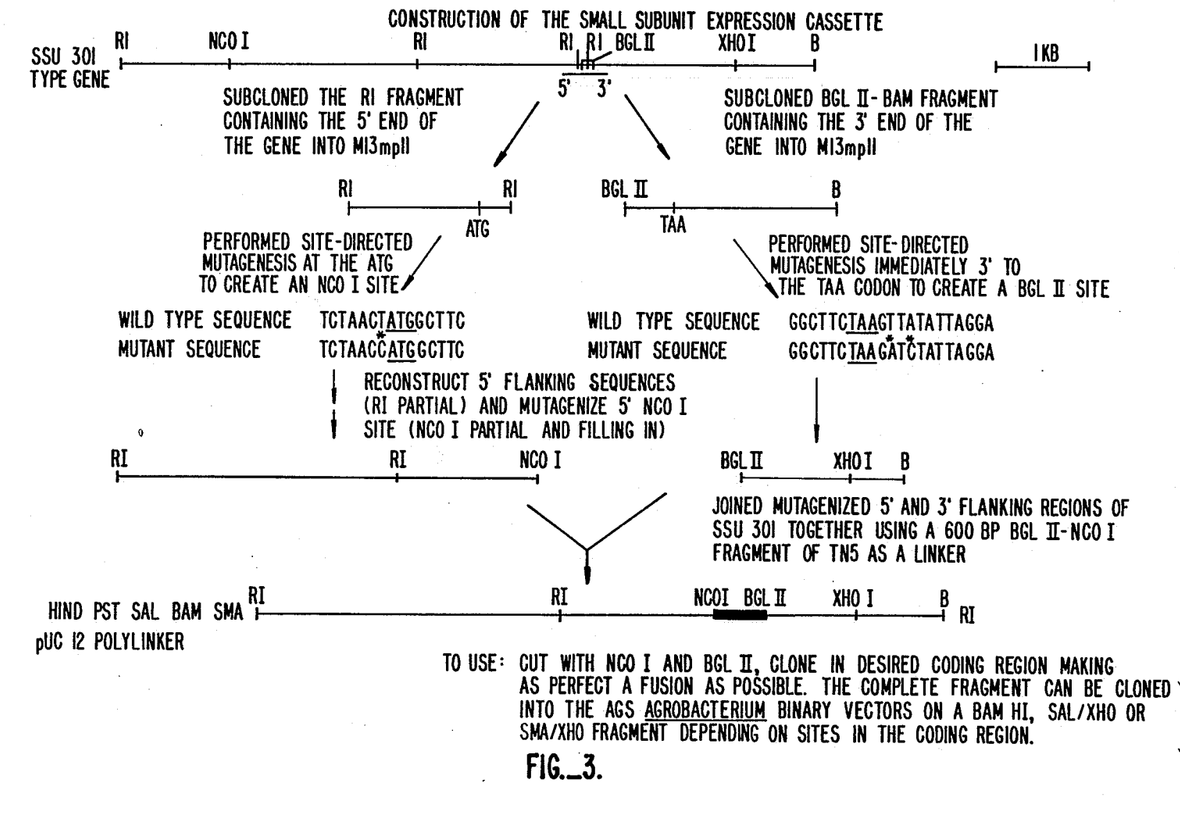
FIG. 3 is a schematic showing the construction of an expression cassette of the invention.

With reference to FIG. 3, an SSU expression cassette (deposited as ATCC #67125) was prepared as follows. Restriction sites were created at the translation start point (NcoI at the ATG) and at the translation stop point (BglII just after the TAA) in the wild-type 302 gene. Two restriction fragments were subcloned from the wild type 301 gene into the bacteriophage M13mpll (J. Messing et al, Nucleic Acid Res., 9, 309–321, 1981). These restriction fragments were a 1.7 kb EcoRI fragment carrying the 5' end of the 301 gene and a 1.8 kb BglII - BamHI fragment carrying the 3' end of the 301 gene. Single-stranded DNA templates of both the 5' and 3' fragments were then isolated from the M13 phage particles and site-directed mutagenesis was carried out using oligonucleotides (the sequences of which contain the desired mutation); M. J. Zoller et al., Nucleic Acid Res., 10, 6487–6500 (1982). The mutations generated are illustrated below.

| | |
|---|---|
| 5' 301 sequence | TCTAACTATGGCTTC |
| 5' mutated sequence | TCTAACCATGGCTTC |
| 3' 301 sequence | GGCTTCTAAGTTATATTAGGA |
| 3' mutated sequence | GGCTTCTAAGATCTATTAGGA |

Reconstruction of the 5kb 5' flanking DNA of the 301 DNA carrying the modification at the ATG was achieved by cloning the EcoRI fragment from the M13 phage into a plasmid (partially digested with EcoRI) carrying the upstream EcoRI fragment which had been modified in order to remove the NcoI site (NcoI digestion, Klenow treatment to fill in the overhanging sticky ends and religation). This cloning generated extra restriction sites at the 5' end of the 5' flanking DNA (from the pUC plasmid linker region) which included a BamHI site. The 5' flanking DNA can therefore be isolated from this plasmid on a BamHI-NcoI restriction fragment.

The 3' flanking DNA can be isolated from the M13 phage clone as a BglII-BamHI restriction fragment. These two fragments carrying the modified 5' and 3' flanking regions were cloned into the plasmid pUC12 using a 600 bp NcoI-BglII fragment of Tn5 as a linker. The Tn5 linker region does not contain any BamHI restriction sites.

To use the expression cassette, the plasmid is digested with the restriction enzymes NcoI and BglII and the desired coding region substituted for the linker fragment. The complete fragment carrying the 5' and 3' flanking regions and the coding region can then be cloned into Agrobacterium vectors on a BamHI, Sal-Xho or Sma-Xho fragment depending on the restriction sites in the coding region.

EXAMPLE VI

Introduction of Foreign Gene into Expression Cassette

In separate experiments, foreign structural genes were introduced into the expression cassette. The genes encoded octopine synthase, chloramphenicol acetyltransferase and chitinase.

A. Octopine synthesis (1) Source and isolation of foreign gene

Octopine synthase (ocs) is an enzyme encoded on the Ti plasmid of octopine-type Agrobacterium strains. It is synthesized in tumors elicited by these strains on susceptible plants and the natural gene has an appropriate nucleotide sequence to constitute a weak, constitutive promoter in plant cells (H. DeGreve et al., *J. Mol. Appl. Genet.*, 1, 499–511, 1983). The gene has been modified to remove all the promoter sequences and form an ocs "cassette" fragment which has been used to assay the strength of promoter sequences (L. Herrera-Estrella et al., *Nature*, 303, 209–213, 1983). If promoter strength is assayed by accumulation of chimaeric mRNA, fusions within the coding region give rise to more chimaeric RNA than the original ocs cassette. For this reason, in order to assay the strength of a chlorophyll a/b binding protein (cab) gene promoter, namely the cab 22L (P. Dunsmuir et al., *Nucleic Acids Res.*, 13, 2503–2518, 1985) promoter, a construction was made in which the fusion point was within the ocs coding sequence. This construction served as the starting point for the ocs construction which was placed in the SSU expression cassette.

(2) Modification of foreign gene

An ocs cassette was cloned as a BamHI fragment into pUC8 so that the 5' end of the ocs gene was towards the PstI site of the pUC linker. Bal31 deletions were generated from the PstI site and BamHI linkers were ligated to the deletion endpoints. A deletion was identified by sequence analysis in which a BamHI linked had been placed near the beginning of the coding sequence. Sequence information is shown below.

| ocs wildtype | ATG GCT AAA GTG GCA ATT |
|---|---|

| ocs deletion #133 | CGGGATCCCGG GCA ATT |
|---|---|

The petunia cab 22L gene (P. Dunsmuir et al., *Nucleic Acids Res.*, 13, 2503–2518, 1985) contains an NcoI site at the translational initiation codon and a PstI site 1 bp downstream (CTGCAG). Cab DNA was linearized at this PstI site, blunt-ended using T4 polymerase and then ligated to BglII linkers (CAGATCTG). The resulting construction was then ligated to ocs deletion #133 (a BglII site can be ligated to a BamHI site). The sequences of the initial cab 22L DNA and the two resulting constructions are shown below.

| cab 22L | AAACC ATG GCT GCA GCT |
|---|---|
| cab 22L-BglII | AAACC ATG GC CAGATCTG |
| cab22L/ocs | AAACC ATG GCC AGA TCC CGG GCA ATT |

The resulting chimaeric cab 22L/ocs construction thus introduces an NcoI site at the ATG of the ocs gene.

A BglII site was introduced immediately downstream of the ocs translation termination codon TGA by oligonucleotide site-directed mutagenesis (M. J. Zoller et al., *Nucleic Acid Res.*, 10, 6487–6500, 1982). Sequence information is shown below.

| ocs 3' sequence | TGGAGTTTGA ATCAAATCTTC |
|---|---|
| ocs 3' mutated sequence | TGGAGTTTGAGATCTAATCTTC |

(3) Construction of the fusion

The ocs coding region was isolated by partial digestion with NcoI (to cleave the created NcoI site at the ATG but not the NcoI site within the coding region) and BglII digestion to cleave the introduced BglII site immediately downstream of the TGA. This was cloned into the SSU expression cassette which had previously been digested with NcoI and BglII. Both the 3' and 5' junctions of the SSU and ocs sequences were confirmed by sequence analysis.

B. Chloramphenicol acetyltransferase (1) Source and isolation of foreign gene Chloramphenicol acetyltransferase (CAT) is an enzyme that catalyzes the formation of acetylated derivatives of the antibiotic chloramphenicol. The gene encoding CAT was cloned from the bacterial transposable element Tn9 (C. M. Gorman et al., *Mol. and Cell. Biol.*, 2, 1044–1045, 1982) and sequenced (N. K. Alton et al., *Nature*, 282, 864–869, 1979).

(2) Modification of foreign gene

Plasmid SV0CAT was used (C.M. Gorman et al., *Mol. and Cell. Biol.*, 2, 1044–1045, 1982). This plasmid carries the CAT coding region on a HindIII - BamHI fragment. This fragment was cloned into the bacteriophage M13, and an NcoI site and a BglII site were introduced at the ATG and TAA respectively by oligonucleotide site directed mutagenesis. Sequence information is shown below.

| 5' CAT sequence | GGAAGCTAAAATGGAGAAAA |
|---|---|
| 5' mutated CAT sequence | GGAAGCTACCATGGAGAAAA |

| | |
|---|---|
| 3' CAT sequence | GGGCGTAA TTTTTTTAAGGC |
| 3' mutated CAT sequence | GGGCGTAAGATCTTTTTAAGGC |

(3) Fusion construction

The CAT coding region (660 bp) was isolated by partial digestion with NcoI (to cleave the introduced site at the ATG but not the NcoI site within the coding region) and BglII digestion to cleave the introduced BglII site immediately downstream of the TAA. This was cloned into the SSU expression cassette which had previously been digested with NcoI and BglII. Both the 3' and 5' junctions of the SSU and CAT sequences were confirmed by sequence analysis.

C. Chitinase

(1) Source and isolation of foreign gene

The isolation of the chiA gene is described in J. Jones et al., *EMBO J.*,5, 467–473 (1985). The gene was isolated from a cosmid library of *Serratia marcescens* by virtue of the fact that the colonies caused clearing zones on chitin plates. A preliminary location of the coding region of the chiA gene on the cosmid was done by a deletion analysis of the cosmid clone and inspection of when the clearing zones on chitin plates disappeared. The accurate localization of the coding region was done by dideoxy sequence analysis.

(2) Modification of foreign gene and fusion construction

Modification of the 5' end of the chiA gene was done in several steps. An NdeI site was introduced at the ATG of the chiA gene by oligonucleotide site-directed mutagenesis (M. J. Zoller et al., *Nucleic Acid Res.*, 10, 6487–6500, 1982). Sequence information is shown below.

| | |
|---|---|
| chiA wild type sequence | GGAATCAGTTATGCGC |
| chiA mutated sequence | GGAATCACATATGCGC (gives an NdeI site at the ATG) |

The chiA gene was cut with NdeI and fused to a nopaline synthase promoter which also had an NdeI site at the ATG. Modifications of the resulting fusion were made using site-directed mutagenesis in order to improve the translation signals. Sequence information is shown below.

| | |
|---|---|
| nos-chiA fusion | TCTGCATATGCGCAAA |
| modified nos-chiA fusion | TCTGAATATGGCCAAA |

The modified nos-chiA fusion generated a BalI restriction site immediately downstream of the ATG. This was used to form a fusion with a chlorophyll a/b binding (Cab 22L) ocs fusion (see Section A of this Example) which had a BalI restriction site overlapping the ATG. Sequence information is shown below.

Cab-chiA fusion AAACCATGGCCAAA

The resulting Cab-chiA fusion generated an NcoI site at the ATG. This was used to fuse the chiA coding region to the 5, end of the SSU expression cassette. Sequence information is shown below.

SSU-chiA fusion TAACCATGGCCAAA

During the construction of the nos-chiA fusion, the chiA coding region fused to the nos 5' sequences was cloned as a BamHI (Klenow treated) EcoRV (partial digestion) fragment into the SmaI site of a pUC vector containing a TaqI fragment (in the AccI site) which carried the nos 3' region. The EcoRV site used was 25 bp downstream of the chiA translation termination codon. This fusion therefore added the nos 3' region onto the 3' end of the chiA coding region, completing the nos-chiA fusion. The resulting plasmid had a BamHI site (from the pUC linker) at the junction of the chiA and nos 3' sequences. This BamHI site was used to fuse the 3' flanking sequences of the SSU expression cassette to the chiA coding sequence (a BamHI site can fuse to a BglII site).

EXAMPLE VII

Plant Transformation with Expression Cassette Containing Foreign Genes

A. Cloning of modified expression cassette into vector

The CAT-SSU fusion was cloned into the binary vector pAGS135 (described in Example IV) on a BamHI fragment, and mobilized into the Agrobacterium strain LBA4404 (A. Hoekema et al., *Nature*, 303, 179–180, 1983). In a separate experiment the same procedure was followed for the chitinase - SSU fusion.

B. Plant transformation

The Agrobacterium strains were co-cultivated with protoplasts isolated from *N.tabacum*. (P. van den Elzen et al., *Plant Molecular Biology*, 5, 149–154, 1985). Transformed protoplasts were selected by their ability to grow on 50mg/1 kanamycin.

C. Expression of the SSU fusions in transformed plants

The transgenic tobacco plants were transferred to the greenhouse once they had established a good root system. They were assayed for expression three weeks after they had been in the greenhouse (previously established to be the time of maximal SSU RNA levels).

(1) CAT expression

The level of CAT RNA in individual transformed plants was assayed by primer extension. In this assay an oligonucleotide specific to the CAT RNA was annealed to total RNA and then extended in a reverse transcriptase reaction back to the 5' end of the message; the amount of extended fragment gave a measure of the levels of CAT RNA in the total RNA. Two of four tobacco transformants assayed, and one of three petunia transformants assayed, showed significant levels of CAT RNA.

(2) Chitinase expression

The level of chitinase RNA in individual transformed plants was assayed by primer extension (as described above). Ten plants were assayed. A range of RNA levels was observed. The relative RNA levels are summarized in the table below; the plant showing the highest levels of chitinase RNA was given the value 100.

TABLE III

| Transformant No. | Relative Chitinase RNA Level |
|---|---|
| 1 | 10 |
| 2 | 100 |
| 3 | 0 |
| 4 | 5 |
| 5 | 11 |
| 6 | 67 |
| 7 | 77 |
| 8 | 0 |
| 9 | 0 |
| 10 | 20 |

A comparison of the chitinase RNA levels from plants transformed with nos-chi, Cab-chi and SSU-chi showed that on average the SSU-chi construct gave 200 times more RNA than the nos-chi constructs. The SSU-chi plant showing the highest chitinase RNA levels (No. 2) gave 15 times more RNA than the highest Cab-chi transformant.

The levels of chitinase protein as assayed by a Western blot (an antibody probe to a nitrocellulose filter carrying the size fractionated polypeptides) were high in six of the initial ten transformants assayed. They correlated with the levels of chitinase RNA observed in the individual transformants. The amount of chitinase protein was evaluated by including a standard dilution series of chitinase protein (isolated from a bacterial strain) on the Western blot. The SSU-chi plant (No. 2) which showed the highest RNA levels accumulated the chitinase protein to 0.1% of the total protein in the leaves.

What is claimed is:

1. An isolated recombinant DNA molecule comprising a DNA promoter sequence capable of directing transcription of downstream foreign structural genes in plants, said sequence comprising less than about 5,000 base pairs of 5' region DNA counted upstream from the translation start site of the Petunia gene for the small subunit ribulose-1, 5-bisphosphate carboxylase and said sequence selected from the group consisting of SSU301 and SSU611.

2. The DNA molecule of claim 1 wherein said sequence is at least 300 base pairs in length.

3. The DNA molecule of claim 1 wherein the sequence has been modified to contain a restriction site at the 3' end of the 5' region DNA.

4. The DNA molecule of claim 3 wherein said sequence is at least 300 base pairs in length.

5. An expression cassette for use in expressing foreign structural genes in plants, said expression cassette comprising
   (a) promoter DNA comprising less than about 5,000 base pairs of 5' region DNA counted upstream from the translation start site of the Petunia gene for the small subunit of ribulose-1, 5-bisphosphate carboxylase, said promoter DNA being modified to create a first restriction site at the 3' end of the 5' region DNA and said promoter DNA selected from the group consisting of SSU301 and SSU611;
   (b) linker DNA fused to said first restriction site; and
   (c) 3' region DNA comprising DNA from the 3' region of a eukaryotic gene, said 3' region DNA having a second restriction site at its 5' end and said 3' region DNA being fused to said linker DNA at said second restriction site.

6. The expression cassette of claim 5 wherein said DNA from the 3' region of a eukaryotic gene is DNA from the 3' region of the gene for the small subunit of Petunia ribulose-1,5bisphosphate carboxylase.

7. The expression cassette of claim 6 wherein said promoter DNA is at least 300 base pairs in length and wherein said DNA from the 3' region of a eukaryotic gene is at least 300 base pairs in length.

8. The expression cassette of claim 5 wherein said first restriction site is an NcoI restriction site and wherein said second restriction site is a BglII restriction site.

9. The expression cassette of claim 5 wherein a foreign structural gene is inserted in place of said linker DNA.

10. An expression vector comprising the expression cassette of claim 5.

11. An expression vector comprising the expression cassette of claim 9.

12. An expression cassette comprising less than about 5,000 base pairs of 5' region DNA counted upstream from the translation start site of the small subunit of Petunia ribulose-1, 5-bisphosphate carboxylase, wherein said 5' region DNA is selected from the group consisting of SSU301 and SSU611.

13. Bacterial strain ATCC #67125.

14. A method of expressing a foreign structural gene in a plant under transcriptional control of a promoter of the small subunit of Petunia ribulose-1,5-bisphosphate carboxylase, comprising
   (a) introducing a foreign structural gene into the expression cassette of claim 12;
   (b) transforming plant cells with a transformation vector comprising the expression cassette into which the foreign structural gene has been introduced;
   (c) growing the plant cells under conditions whereby the foreign structural gene is expressed under transcriptional control of the 5' region DNA of the small subunit of Petunia ribulose-1,5-bisphosphate carboxylase.

* * * * *